W. A. WARRINER
ROSE PLANT
Filed Sept. 23, 1974
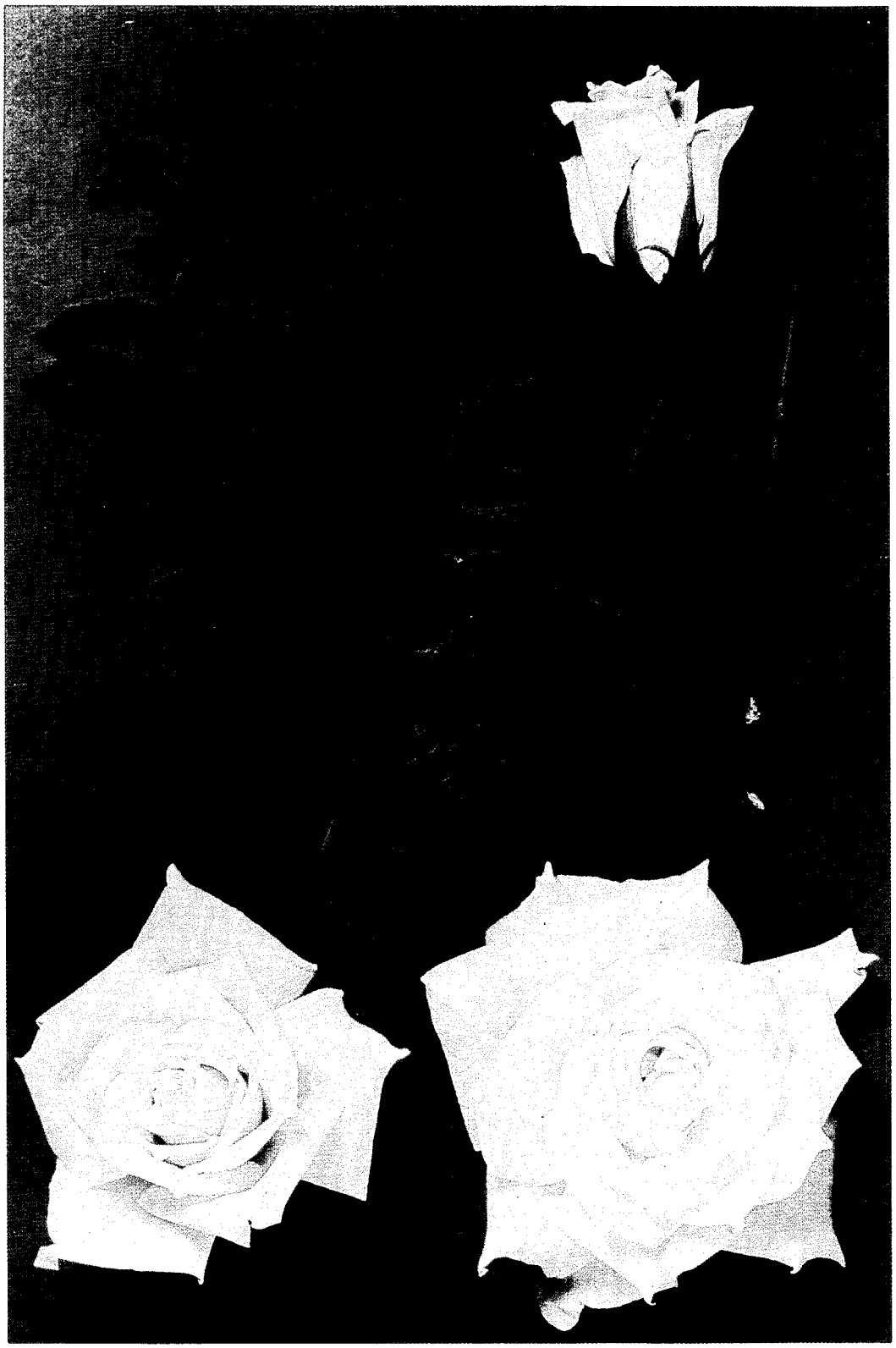

United States Patent

Plant Pat. 3,791
Patented Sept. 23, 1975

3,791
ROSE PLANT

William A. Warriner, Tustin, Calif., assignor to Jackson and Perkins Company, Medford, Oreg.

Filed Sept. 23, 1974, Ser. No. 508,699
Int. Cl. A01h *5/00*
U.S. Cl. Plt.—15 1 Claim

The present invention relates to a new and distinct cultivar of rose plant of the hybrid tea class which was originated by me by crossing the cultivar Golden Sun, unpatented, with pollen from the cultivar South Seas, U.S. Plant Pat. No. 2,184.

The primary objective of this breeding was to produce a new rose cultivar of vigorous growth which would be suitable as a garden cultivar as well as a greenhouse cultivar for the production of yellow blooms.

This objective was substantially achieved along with other desirable improvements as evidenced by the following unique combination of characteristics which are outstanding in the new cultivar and which distinguish it from its parents as well as from all other cultivars of which I am aware:

1. A vigorous, well branched plant habit.
2. Very few prickles.
3. Large buds of Buttercup Yellow opening to large blooms of Lemon Yellow.
4. A high degree of resistance to powdery mildew.
5. Large, semi-glossy foliage.
6. Little or no fragrance.
7. Relatively good production of blooms when grown in a greenhouse.

Asexual reproduction of this new cultivar by budding, as performed at Wasco, Calif., proves that the foregoing characteristics and distinctions reproduce true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

Parentage: Seedling.
*Seed parent.*—Golden sun, unpatented.
*Pollen parent.*—South Seas, U.S. Plant Pat. No. 2,184.
Classification:
*Botanic.*—Rosa hybrid.
*Commercial.*—Hybrid tea.

FLOWER

Observations were made at Irvine, Calif., in early June from plants grown in a greenhouse.

Blooming habit: Recurrent—continuous.
Bud:
*Size.*—1½ inches when petals start to unfurl.
*Form.*—Pointed ovoid.
*Color.*—When sepals first divide between Chrome Yellow (605/1) and Buttercup Yellow (5/1). When half bloom; upper side of petals near Buttercup Yellow (5); lower side of petals near Buttercup Yellow (5/1).
*Sepals.*—Color: Outer surface Scheeles Green (860/2). Inner surface only lightly covered with tomentum. Three appendaged sepals lightly appendaged. Two unappendaged sepals serrated, hairy edged.

*Receptacle.*—Color: Scheeles Green (860/1). Shape: Funnel. Size: Large. Surface: Smooth.
*Peduncle.*—Length: Long. Surface: Smooth. Color: Light Green. Strength: Stiff.
*Opening.*—Tips and edges curl lightly.
Bloom:
*Size.*—Large. Average open size 4½ inches to 5 inches.
*Borne.*—Singly and in clusters on large new canes.
*Stems.*—Long.
*Form.*—When first open—high centered. Permanence—outer petal edges slightly curled.
*Petalage.*—Number of petals under normal conditions, 25–35.
*Color.*—Center of flower: Upper side of petals near Lemon Yellow (4/1). Reverse side of petals near Lemon Yellow (4/2). Base of petals near Lemon Yellow (4/1). General tonality from a distance Lemon Yellow (4/1).
*Discoloration.*—At end of first day—no change. Fourth or fifth day—color lightens to Aureolin (3/2).
*Fragrance.*—Slight.
*Petals.*—Texture: Thick. Shape: Round. Form: Edges slightly quilled to moderately quilled.
*Arrangement.*—Loosely imbricated. Petaloids in center—few.
*Persistence.*—Drop off cleanly.
*Lastingness.*—On the plant—long. As cut flower—long.
Reproductive parts:
*Anthers.*—Large. Color—yellow. Arrangement—regular around styles.
*Filaments.*—Color—yellow.
*Pollen.*—Gold yellow.
*Styles.*—Color—light yellow suffused with pink.
*Stigmas.*—Color—yellow.

PLANT

Form: Bush.
Growth: Vigorous, upright, branching.
Foliage: Number of leaflets on normal mid-stem leaves, usually 5.
*Size.*—Large.
*Quantity.*—Normal.
*Color.*—New foliage: Garnet Brown (00918/3) suffused with Scheeles Green (860). Old foliage: Near Parsley Green (00962/1).
Leaflets:
*Shape.*—Oval, pointed.
*Texture.*—Upper side—semi-glossy.
*Edge.*—Serrated, slightly undulated.
*Serration.*—Single, small.
*Petiole.*—Rachis—Color—Green. Underside smooth.
*Stipules.*—Long.
*Disease resistance.*—Resistant to mildew under normal growing conditions at Irvine, Calif.
Wood:
*New wood.*—Color—Light green. Bark—smooth.
*Old wood.*—Color—Green. Bark—smooth.
Prickles:
*Quantity.*—On main stalks from base—few. On laterals from stalk—few.
*Form.*—Broad base, medium hooked downward.
*Color when young.*—Brown.
*Position.*—Irregular.
Small prickles:
*Quantity.*—On main stalks—very few. On laterals—very few.
*Color.*—Brown.

I claim:

1. A new and distinct variety of rose plant of the hybrid tea class, substantially as herein shown and described, characterized particularly as to novelty by its vigorous well branched plant habit, by its formation of large buds of Buttercup Yellow opening to large blooms of Lemon Yellow having little or no fragrance, large semi-glossy foliage, a high degree of resistance to powdery mildew, and relatively good production of blooms when grown in a greenhouse.

No references cited.

ROBERT E. BAGWILL, Primary Examiner